United States Patent
Frank et al.

(10) Patent No.: US 8,415,485 B2
(45) Date of Patent: Apr. 9, 2013

(54) PROCESSES FOR THE PREPARATION OF 2-(1-PHENYLETHYL)ISOINDOLIN-1-ONE COMPOUNDS

(75) Inventors: Anthony J. Frank, Easton, PA (US); Hon-Wah Man, Princeton, NJ (US); Chuansheng Ge, Belle Mead, NJ (US); Manohar Saindane, Monmouth Junction, NJ (US)

(73) Assignee: Celgene Corporation, Summit, NJ (US)

( * ) Notice: Subject to any disclaimer, the term of this patent is extended or adjusted under 35 U.S.C. 154(b) by 124 days.

(21) Appl. No.: 12/901,338

(22) Filed: Oct. 8, 2010

(65) Prior Publication Data

US 2011/0087033 A1   Apr. 14, 2011

Related U.S. Application Data

(60) Provisional application No. 61/250,421, filed on Oct. 9, 2009.

(51) Int. Cl.
*C07D 209/46* (2006.01)

(52) U.S. Cl.
USPC .......................... 548/415; 548/451; 548/469

(58) Field of Classification Search .................. 548/451
See application file for complete search history.

(56) References Cited

U.S. PATENT DOCUMENTS

| 7,034,052 B2 * | 4/2006 | Man et al. ..................... 514/429 |
| 2004/0254214 A1 | 12/2004 | Man et al. |
| 2006/0084815 A1 | 4/2006 | Muller et al. |
| 2010/0129363 A1 | 5/2010 | Zeldis et al. |

FOREIGN PATENT DOCUMENTS

WO   WO 2004/060313   7/2004

* cited by examiner

*Primary Examiner* — Shawquia Young
(74) *Attorney, Agent, or Firm* — Jones Day

(57) ABSTRACT

Methods for preparation of isoindolin-1-one compounds are described.

17 Claims, No Drawings

PROCESSES FOR THE PREPARATION OF 2-(1-PHENYLETHYL)ISOINDOLIN-1-ONE COMPOUNDS

This application claims the benefit of U.S. Provisional Application No. 61/250,421, filed Oct. 9, 2009, the entirety of which is incorporated herein by reference.

1. FIELD

Provided herein are processes for the preparation of 2-(1-phenylethyl)isoindolin-1-one compounds useful for reducing levels or activity of tumor necrosis factor α in mammals. Such 2-(1-phenylethyl)isoindolin-1-one compounds include 7-nitro-2-[1-(3-ethoxy-4-methoxyphenyl)-2-(methylsulfonyl)ethyl]isoindolin-1-one, 7-amino-2-[1-(3-ethoxy-4-methoxyphenyl)-2-(methylsulfonyl)ethyl]isoindolin-1-one, and cyclopropyl-N-{2-[1-(3-ethoxy-4-methoxyphenyl)-2-(methylsulfonyl)ethyl]-3-oxoisoindolin-4-yl}carboxamide.

2. BACKGROUND

Tumor necrosis factor α, or TNF-α, is a cytokine which is released primarily by mononuclear phagocytes in response to a number immunostimulators. When administered to animals or humans, it can cause inflammation, fever, cardiovascular effects, hemorrhage, coagulation, and acute phase responses similar to those seen during acute infections and shock states. Excessive or unregulated TNF-α production thus has been implicated in a number of disease conditions. These disease conditions include endotoxemia and/or toxic shock syndrome (Tracey et al., *Nature* 330, 662-664 (1987) and Hinshaw et al., *Circ. Shock* 30, 279-292 (1990)); rheumatoid arthritis, Crohn's disease, cachexia (Dezube et al., *Lancet*, 335(8690), 662 (1990)) and Adult Respiratory Distress Syndrome (ARDS) where TNF-α concentration in excess of 12,000 pg/mL have been detected in pulmonary aspirates from ARDS patients (Millar et al., *Lancet* 2(8665), 712-714 (1989)). Systemic infusion of recombinant TNF-α also resulted in changes typically seen in ARDS (Ferrai-Baliviera et al., *Arch. Surg.* 124(12), 1400-1405 (1989)). Certain 2-(1-phenylethyl)isoindolin-1-one compounds have been shown to reduce levels of TNF-α in the literature such as U.S. Pat. Nos. 6,667,316 and 6,020,358 and U.S. Patent Publication Nos. 2004/0254214 and 2004/0204448, all of which are incorporated herein by reference in their entirety.

Existing methods for synthesizing 2-(1-phenylethyl)isoindolin-1-one compounds have been described in U.S. Pat. Nos. 6,667,316 and 6,020,358 and U.S. Patent Publication Nos. 2004/0254214 and 2004/0204448. While these methods are useful for preparing 2-(1-phenylethyl)isoindolin-1-one compounds, alternative methods for the preparation of 2-(1-phenylethyl)isoindolin-1-one compounds, particularly for manufacturing scale production, are desirable.

Citation of any reference in Section 2 of this application is not to be construed as an admission that such reference is prior art to the present application.

3. SUMMARY

Provided herein are efficient processes for the preparation of 2-(1-phenylethyl)isoindolin-1-one compounds, such as 7-nitro-2-[1-(3-ethoxy-4-methoxyphenyl)-2-(methylsulfonyl)ethyl]isoindolin-1-one, 7-amino-2-[1-(3-ethoxy-4-methoxyphenyl)-2-(methylsulfonyl)ethyl]isoindolin-1-one, and cyclopropyl-N-{2-[1-(3-ethoxy-4-methoxyphenyl)-2-(methylsulfonyl)ethyl]-3-oxoisoindolin-4-yl}carboxamide.

In one aspect, provided herein is a process for preparing an isoindolin-1-one compound of Formula (I):

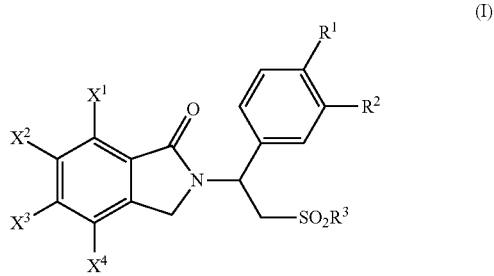

or a pharmaceutically acceptable salt or solvate or polymorph thereof, comprising the step of reacting a primary amine of Formula (II):

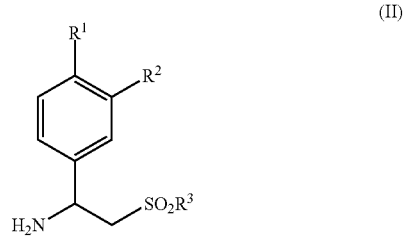

or a salt thereof with a 2-(bromomethyl)benzoic acid ester of Formula (III):

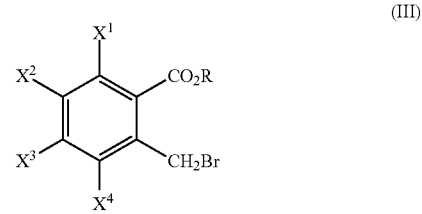

in the presence of an inorganic base, wherein
R is alkyl or aryl;
each of $R^1$ and $R^2$ is independently hydrogen, alkyl of 1 to 4 carbon atoms, alkoxy of 1 to 4 carbon atoms, cyano, or cycloalkoxy of 3 to 18 carbon atoms;
$R^3$ is hydroxy, alkyl of 1 to 8 carbon atoms, phenyl, benzyl, or $NR^4R^5$;
each of $X^1$, $X^2$, $X^3$ and $X^4$ is independently hydrogen, halo, alkyl of 1 to 4 carbon atoms, alkoxy of 1 to 4 carbon atoms, nitro, cyano, hydroxy, or $-NR^4R^5$; or any two of $X^1$, $X^2$, $X^3$ and $X^4$ on adjacent carbon atoms, together with the depicted phenylene ring are naphthylidene;
each of $R^4$ and $R^5$ is independently hydrogen, alkyl of 1 to 8 carbon atoms, phenyl, or benzyl; or one of $R^4$ and $R^5$ is hydrogen and the other is $-COR^6$, or $-SO_2R^6$; or $R^4$ and $R^5$ taken together are tetramethylene, pentamethylene, hexamethylene, or $-CH_2CH_2X^5CH_2CH_2-$ in which $X^5$ is $-O-$, $-S-$ or $-NH-$;
each of $R^{4'}$ and $R^{5'}$ is independently hydrogen, alkyl of 1 to 8 carbon atoms, phenyl, or benzyl; or one of $R^{4'}$ and $R^{5'}$ is hydrogen and the other is $-COR^{6'}$, or $-SO_2R^{6'}$; or $R^{4'}$ and $R^{5'}$ taken together are tetramethylene, pentamethylene, hexamethylene, or —$CH_2CH_2X^{5'}CH_{21}CH_2$— in which $X^5$ is —O—, —S— or —NH—; and each of $R^6$ and $R^{6\alpha}$ is independently hydrogen, alkyl of 1 to 8 carbon atoms, cycloalkyl of 3 to 8 carbon atoms, or phenyl.

In some embodiments, each of $R^1$ and $R^2$ in Formula (I) is independently alkoxy of 1 to 4 carbon atoms. In a particular embodiment, $R^1$ is methoxy and $R^2$ is ethoxy. In other embodiments, each of $X^2$, $X^3$ and $X^4$ in Formula (I) is hydrogen; and $X^1$ is nitro, —$NH_2$ or —$NHCOR^{6'}$ where $R^{6'}$ is hydrogen, alkyl of 1 to 8 carbon atoms, cycloalkyl of 3 to 8 carbon atoms, or phenyl. In one embodiment, $X^1$ is —NHCOR$^6$ and $R^{6'}$ is cyclopropyl. In some embodiments, $R^3$ is methyl. In another embodiment, R is methyl.

In a particular embodiment, the isoindolin-1-one compound of Formula (I) is 7-nitro-2-[1-(3-ethoxy-4-methoxyphenyl)-2-(methylsulfonyl)ethyl]isoindolin-1-one, where $X^1$ is nitro; each of $X^2$, $X^3$ and $X^4$ is hydrogen; $R^3$ is methyl; $R_1$ is methoxy; and $R_2$ is ethoxy.

In another embodiment, the isoindolin-1-one compound of Formula (I) is 7-amino-2-[1-(3-ethoxy-4-methoxyphenyl)-2-(methylsulfonyl)ethyl]isoindolin-1-one where $X^1$ is —$NH_2$; each of $X^2$, $X^3$ and $X^4$ is hydrogen; $R^3$ is methyl; $R_1$ is methoxy; and $R_2$ is ethoxy.

In another embodiment, the isoindolin-1-one compound of Formula (I) is cyclopropyl-N-{2-[1-(3-ethoxy-4-methoxyphenyl)-2-(methylsulfonyl)ethyl]-3-oxoisoindolin-4-yl}carboxamide where $X^1$ is NHCO-cyclopropyl; each of $X^2$, $X^3$ and $X^4$ is hydrogen; $R^3$ is methyl; $R_1$ is methoxy; and $R_2$ is ethoxy.

4. DETAILED DESCRIPTION

4.1 Definitions

As used herein and unless otherwise indicated, the term "halo," "halogen" or the like means —F, —Cl, —Br or —I.

As used herein and unless otherwise indicated, the term "alkyl" or "alkyl group" means a univalent saturated branched or straight hydrocarbon chain containing from 1 to 8 carbon atoms. Non-limiting examples of such alkyl groups are methyl, ethyl, propyl, isopropyl, butyl, isobutyl, sec-butyl, tert-butyl, pentyl, hexyl, heptyl and octyl. An alkyl group can be unsubstituted or substituted with one or more suitable substituents.

As used herein and unless otherwise indicated, the term "alkoxy" or "alkoxy group" means an alkyl group bound to the remainder of the molecule through an ethereal oxygen atom. Non-limiting examples of such alkoxy groups are methoxy, ethoxy, propoxy, isopropoxy, butoxy, isobutoxy, sec-butoxy, and tert-butoxy. An alkoxyl group can be unsubstituted or substituted with one or more suitable substituents.

As used herein and unless otherwise indicated, the term "cycloalkyl" or "cycloalkyl group" means a univalent cyclic hydrocarbon chain which may be saturated or unsaturated. Unless otherwise stated, such chains can contain from 3 to 18 carbon atoms and include monocycloalkyl, polycycloalkyl, and benzocycloalkyl structures. Monocycloalkyl refers to groups having a single ring group. Polycycloalkyl denotes hydrocarbon systems containing two or more ring systems with one or more ring carbon atoms in common; i.e., a spiro, fused, or bridged structure. Benzocycloalkyl signifies a monocyclic alkyl group fused to a benzo group. Non-limiting examples of monocycloalkyl groups are cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Non-limiting examples of polycycloalkyl include decahydronaphthalene, spiro[4.5]decyl, bicyclo[2.2.1]heptyl, bicyclo[3.2.1]octyl, pinanyl, norbornyl, and bicyclo[2.2.2]octyl. Non-limiting examples of benzocycloalkyl include tetrahydronaphthyl, indanyl, and 1.2-benzocycloheptanyl. A cycloalkyl group can be unsubstituted or substituted with one or more suitable substituents.

As used herein and unless otherwise indicated, the term "cycloalkoxy" or "cycloalkoxy group" means a cycloalkyl group as described above, that is a monocycloalkyl, polycycloalkyl, or benzocycloalkyl structure, bound to the remainder of the molecule through an ethereal oxygen atom. A cycloalkoxy group can be unsubstituted or substituted with one or more suitable substituents.

As used herein and unless otherwise indicated, the term "substituted" as used to describe a compound or chemical moiety means that at least one hydrogen atom of that compound or chemical moiety is replaced with a second chemical moiety. The second chemical moiety can be any suitable substituent that does not nullify the synthetic or pharmaceutical utility of the compounds provided herein or the intermediates useful for preparing them. Examples of suitable substituents include, but are not limited to: alkyl; alkenyl; alkynyl; aryl; cycloalkyl; alkoxy; CN; OH; halo, C(O)OH; COhalo; O(CO)halo; $CF_3$, $N_3$; $NO_2$, NH(alkyl); N(alkyl)$_2$; NH(aryl); N(aryl)$_2$; (CO)NH$_2$; (CO)NH(alkyl); (CO)N(alkyl)$_2$; (CO)NH(aryl) and (CO)N(aryl)$_2$. One of skill in art can readily choose a suitable substituent based on the stability and pharmacological and synthetic activity of the compound provided herein.

As used herein and unless otherwise indicated, a composition that is "substantially free" of a compound means that the composition contains less than about 20% by weight, more preferably less than about 10% by weight, even more preferably less than about 5% by weight, and more preferably less than about 3% by weight of the compound.

As used herein and unless otherwise indicated, the term "stereochemically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and more preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein and unless otherwise indicated, the term "racemic" or "racemate" means about 50% of one enantiomer and about 50% of the corresponding enantiomer relative to all chiral centers in the molecule. Compounds provided herein encompass all enantiomerically pure, enantiomerically enriched, diastereomerically pure, diastereomerically enriched, and racemic mixtures of the compounds.

As used herein and unless otherwise indicated, the term "process(es) for preparing" or "process(es) for the preparation" refers to the methods disclosed herein which are useful for preparing a compound provided herein. Modifications to the methods disclosed herein (e.g., starting materials, reagents, protecting groups, solvents, temperatures, reaction times, purification) are also encompassed.

As used herein and unless otherwise indicated, the term "adding", "reacting" or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein and unless otherwise indicated, a reaction that is "substantially complete" or is driven to "substantial completion" means that the reaction contains more than about 80% by percent yield, more preferably more than about 90% by percent yield, even more preferably more than about 95% by percent yield, and more preferably more than about 97% by percent yield of the desired product.

As used herein and unless otherwise indicated, the term "pharmaceutically acceptable salt" includes, but is not limited to, salts of acidic or basic groups that may be present in the compounds provided herein. Compounds provided herein that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochioride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds provided herein that include an amino group also can form pharmaceutically acceptable salts with various amino acids, in addition to the acids mentioned above. Compounds provided herein that are acidic in nature are capable of forming base salts with various pharmacologically acceptable cations. Non-limiting examples of such salts include alkali metal or alkaline earth metal salts and, particularly, calcium, magnesium, sodium, lithium, zinc, potassium, and iron salts.

As used herein and unless otherwise indicated, the term "hydrate" means a compound provided herein, or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate, and the like).

As used herein and unless otherwise indicated, the term "polymorph" means solid crystalline forms of a compound provided herein or complex thereof. Different polymorphs of the same compound can exhibit different physical, chemical and/or spectroscopic properties.

As used herein and unless otherwise indicated, the phrase "diseases or conditions related to an abnormally high level or activity of TNF-α" means diseases or conditions that would not arise, endure or cause symptoms if the level or activity of TNF-α were lower, or diseases or conditions that can be prevented or treated by a lowering of TNF-α level or activity.

As used herein, and unless otherwise specified, the terms "treat," "treating" and "treatment" contemplate an action that occurs while a patient is suffering from the specified disease or disorder, which reduces the severity or symptoms of the disease or disorder or retards or slows the progression or symptoms of the disease or disorder.

Acronyms or symbols for groups or reagents have the following definition: HPLC=high performance liquid chromatography, $CH_3CN$=acetonitrile; DMF=dimethyl formamide, DMSO=dimethyl sulfoxide, THF=tetrahydrofuran, $CH_3OAc$=methyl acetate, EtOAc=ethyl acetate, AIBN=2.2'-azobisisobutyronitrile, DBH=1,3-dibromo-5,5-dimethylhydantoin and DIPEA=N,N-diisopropylethylamine.

If there is a discrepancy between a depicted structure and a name given that structure, the depicted structure is to be accorded more weight. Furthermore, if the stereochemistry of a structure or a portion thereof is not indicated, e.g., with bold or dashed lines, the structure or portion thereof is to be interpreted as encompassing any or all stereoisomers of it.

The processes provided herein can be understood more fully by reference to the following detailed description and illustrative examples, which are intended to exemplify non-limiting embodiments.

4.2 Processes

Provided herein are processes for the preparation of 2-(1-phenylethyl)isoindolin-1-one compounds. In certain embodiments, the processes provided herein are to encompass efficient means for the large scale or commercial production of 2-(1-phenylethyl)isoindolin-1-one compounds.

In some embodiments of interest, provided herein are processes for preparing isoindolin-1-one compounds of Formula (I):

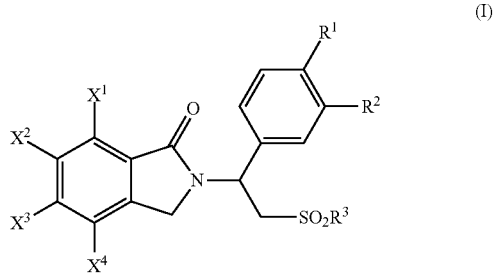

or pharmaceutically acceptable salts, solvates including hydrates or polymorphs thereof, comprising the step of reacting a primary amine of Formula (II):

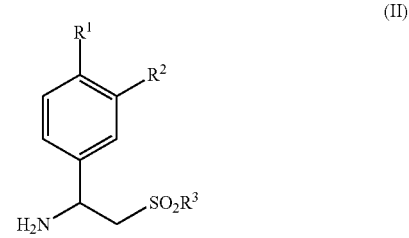

or a salt thereof with a 2-(bromomethyl)benzoic acid ester of Formula (III):

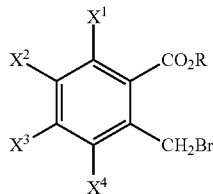

(III)

in the presence of an inorganic base, wherein
R is alkyl or aryl;
each of $R^1$ and $R^2$ is independently hydrogen, alkyl of 1 to 4 carbon atoms, alkoxy of 1 to 4 carbon atoms, cyano, or cycloalkoxy of 3 to 18 carbon atoms;
$R^3$ is hydroxy, alkyl of 1 to 8 carbon atoms, phenyl, benzyl, or $NR^4R^5$;
each of $X^1$, $X^2$, $X^3$ and $X^4$ is independently hydrogen, halo, alkyl of 1 to 4 carbon atoms, alkoxy of 1 to 4 carbon atoms, nitro, cyano, hydroxy, or —$NR^{4'}R^{5'}$; or any two of $X^1$, $X^2$, $X^3$ and $X^4$ on adjacent carbon atoms, together with the depicted phenylene ring are naphthylidene;
each of $R^4$ and $R^5$ is independently hydrogen, alkyl of 1 to 8 carbon atoms, phenyl, or benzyl; or one of $R^4$ and $R^5$ is hydrogen and the other is —$COR^6$, or —$SO_2R^6$; or $R^4$ and $R^5$ taken together are tetramethylene, pentamethylene, hexamethylene, or —$CH_2CH_2X^5CH_2CH_2$— in which $X^5$ is —O—, —S— or —NH—;
each of $R^{4'}$ and $R^{5'}$ is independently hydrogen, alkyl of 1 to 8 carbon atoms, phenyl, or benzyl; or one of $R^{4'}$ and $R^{5'}$ is hydrogen and the other is —$COR^{6'}$, or —$SO_2R^{6'}$; or $R^{4'}$ and $R^{5'}$ taken together are tetramethylene, pentamethylene, hexamethylene, or —$CH_2CH_2X^5CH_2CH_2$— in which $X^5$ is —O—, —S— or —NH—; and
each of $R^6$ and $R^{6'}$ is independently hydrogen, alkyl of 1 to 8 carbon atoms, cycloalkyl of 3 to 8 carbon atoms, or phenyl.

Any inorganic base that can catalyze or promote the nucleophilic substitution reaction between a benzylic bromide and a primary amine, such as the initial reaction between Formula (II) and Formula (III), can be used. Non-limiting examples of suitable inorganic bases include metal hydroxides such as potassium hydroxide and sodium hydroxide, metal carbonates such as potassium carbonate and sodium carbonate, metal hydrogen carbonates such as sodium hydrogen carbonate and potassium hydrogen carbonate, metal hydrides and combinations thereof In one embodiment, the inorganic base is sodium hydrogen carbonate. In another embodiment, the inorganic base is potassium carbonate. The mole ratio of the inorganic base to Formula (I) can be in the range of about 1:1 to about 3:1. In some embodiments, the mole ratio of the inorganic base to Formula (I) is about 1.5:1 to about 2.5:1. In other embodiments, the mole ratio of the inorganic base to Formula (I) is about 2.0:1 to about 2.2:1.

The reaction between Formula (II) and Formula (III) can occur in a solvent such as acetonitrile, ethyl acetate, ketones such as acetone and methyl ethyl ketone, ethers such as diethyl ether and tetrahydrofuran, dichloromethane, chloroform, N-methyl pyrrolidinone, dimethyl formamide, dimethyl sulfoxide, and combinations thereof. In general, the choice of a suitable solvent can be based on many factors such as the solubility of the inorganic base in the solvent, the basicity or acidity of the solvent, and the solvent effect on the basicity of the inorganic base. In one embodiment, the solvent is acetonitrile and the inorganic base is potassium carbonate. In another embodiment, the solvent is dimethyl formamide and the inorganic base is sodium hydrogen carbonate.

The reaction temperature can be any temperature useful for the reaction between Formula (II) and Formula (III) according to a person of ordinary skill in the art. For instance, in certain embodiments, the reaction temperature is between about 20° C. and about 120° C. In some embodiments of interest, the reaction temperature is between about 50° C. and about 100° C. In other embodiments of interest, the reaction temperature is between about 70° C. and about 100° C. In a particular embodiment, the solvent is acetonitrile and the reaction temperature is the boiling point of acetonitrile, i.e., 81-82° C.

The reaction time can be any time useful for the reaction between Formula (II) and Formula (III) according to a person of ordinary skill in the art. In general, the higher the reaction temperature, the shorter is the reaction time. For instance, in certain embodiments, the reaction time is from about 1 to about 24 hours. In some embodiments of interest, the reaction time is between about 1 and about 5 hours. In a particular embodiment of interest, the reaction time is about 2 to 4 hours at 81-82° C.

The ratio of the 2-(bromomethyl)benzoic acid ester of Formula (III) to the primary amine of Formula (II) can be any mole ratio useful for the reaction between Formula (II) and Formula (III) according to a person of ordinary skill in the art. For instance, in certain embodiments, the mole ratio of Formula (III) to Formula (II) can be between about 1:0.8 and about 1:1.3. In other embodiments, the mole ratio of Formula (III) to Formula (II) is between about 1:0.9 and about 1:1.2. In further embodiments, the mole ratio of Formula (III) to Formula (II) is between about 1:1 and about 1:1.1.

If a racemic mixture of Formula (I) is desired, a racemic mixture of Formula (II) can be used. Conversely, if an enantiomerically pure Formula (I) is desired, an enantiomerically pure Formula (II) can be used. Some non-limiting examples of Formula (II) include (1S)-1-(3-ethoxy-4-methoxyphenyl)-2-methanesulfonyl-ethylamine and (1R)-1-(3-ethoxy-4-methoxyphenyl)-2-methanesulfonyl-ethylamine. Alternatively, if an enantiomerically pure Formula (I) is desired, a racemic mixture of Formula (I) can be prepared and then resolved into the enantiomers by conventional resolution techniques such as biological resolution and chemical resolution. In general, biological resolution uses a microbe which metabolizes one specific enantiomer leaving the other enantiomer alone. In chemical resolution, the racemic mixture is converted into two diastereoisomers that can be separated by conventional techniques such as fractional crystallization and chromatographies. Once separated, the diasteriosomeric forms can be converted separately back to the enantiomers. In one embodiment, the isoindolin-1-one compound of Formula (I) is a racemic mixture. In another embodiment, the isoindolin-1-one compound of Formula (I) is the (+)-enantiomer. In a further embodiment, the isoindolin-1-one compound of Formula (I) is the (−)-enantiomer.

In some embodiments of the isoindolin-1-one compounds of Formula (I), each of $R^1$ and $R^2$ is independently alkoxy of 1 to 4 carbon atoms. In a particular embodiment, $R^1$ is methoxy and $R^2$ is ethoxy. In other embodiments, each of $X^2$, $X^3$ and $X^4$ is hydrogen; and $X^1$ is nitro, —$NH_2$ or —$NHCOR^{6'}$ where $R^{6'}$ is hydrogen, alkyl of 1 to 8 carbon atoms, cycloalkyl of 3 to 8 carbon atoms, or phenyl. In one embodiment, $X^1$ is —$NHCOR^{6'}$ and $R^{6'}$ is cyclopropyl. In some embodiments, $R^3$ is methyl. In another embodiment, R is methyl.

In a particular embodiment, the isoindolin-1-one compound of Formula (I) is Compound (1), i.e., (1S)-7-nitro-2-[1-(3-ethoxy-4-methoxyphenyl)-2-(methylsulfonyl)ethyl]isoindolin-1-one, where $X^1$ is nitro; each of $X^2$ $X^3$ and $X^4$ is hydrogen; $R^3$ is methyl; $R_1$ is methoxy; and $R_2$ is ethoxy. Referring to Scheme A below, Compound (1) can be prepared from reaction between Compound (2) (i.e., (1S)-1-(3-ethoxy-4-methoxyphenyl)-2-methanesulfonyl-ethylamine) and Compound (3) (i.e., methyl 2-bromomethyl-6-nitrobenzoate) in the presence of an inorganic catalyst such as potassium carbonate and sodium hydrogen carbonate. In another embodiment, the (1S)-1-(3-ethoxy-4-methoxyphenyl)-2-methanesulfonyl-ethylamine) is replaced with (1R)-1-(3-ethoxy-4-methoxyphenyl)-2-methanesulfonyl-ethylamine) to form (1N)-7-nitro-2-[1-(3-ethoxy-4-methoxyphenyl)-2-(methylsulfonyl)ethyl]isoindolin-1-one.

SCHEME A

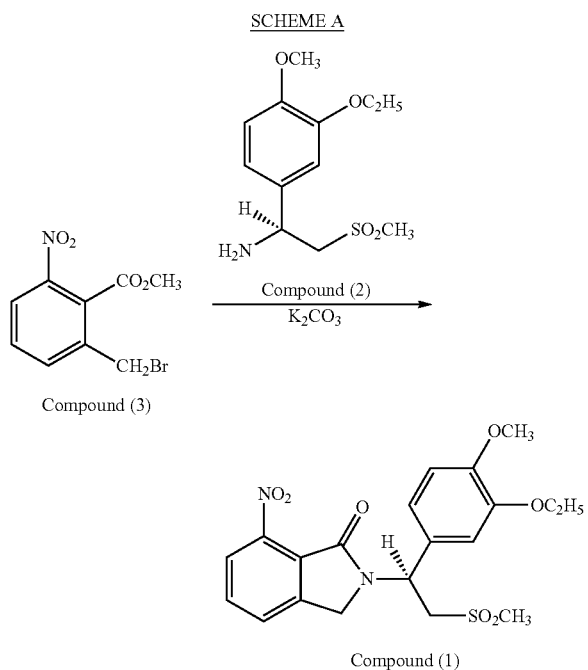

The reaction between Compound (2) and Compound (3) can occur in a solvent. In some embodiments, the solvent is acetonitrile, the reaction time is about 1 to 24 hours and the inorganic catalyst is potassium carbonate. In other embodiments, the reaction time is about 2 to 4 hours and the reaction occurs in refluxing acetonitrile. In further embodiments, the reaction occurs in DMF for about 15-18 hours at about 70-100° C. in the presence of sodium hydrogen carbonate.

Optionally, the isoindolin-1-one compound of Formula (I) can be converted into an acid salt by reacting Formula (I) with an acid in a mole ratio of, for example, about 1:1. Non-limiting examples of suitable acids include methanesulfonic acid, trifluoroacetic acid, 4-(trifluoromethyl)benzoic acid, p-toluenesulfonic acid, hydrochloric acid, nitric acid, sulfuric acid and phosphoric acid. In one embodiment, the isoindolin-1-one compound of Formula (I) is converted into a hydrochloride salt with 12N hydrochloric acid at a temperature between about 0° C. and about 22° C.

The primary amine of Formula (II) can be prepared by the reaction between a sulfone and a benzaldehyde derivative and other methods known in the art. The reactions between sulfones and benzaldehyde derivatives have been disclosed in U.S. Pat. No. 6,020,358 and U.S. Patent Publication No. 2004/0204448, both of which are incorporated herein by reference.

The 2-(bromomethyl)benzoic acid ester of Formula (III) can be prepared by any method known to a person of ordinary skill in the art. In certain embodiments, the 2-(bromomethyl)benzoic acid ester of Formula (III) can be prepared by reacting a 2-methylbenzoic acid ester of Formula (IV):

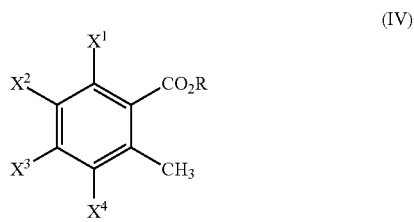

with a brominating agent, wherein R, $X^1$, $X^2$, $X^3$ and $X^4$ are defined as above.

The brominating agent can be any known brominating agent that can substitute a benzylic hydrogen with a bromo group. Non-limiting examples of suitable brominating agents include 1,3-dibromo-5,5-dimethylhydantoin, N-bromosuccinimide, bromotrichloromethane, a bromine complex of styrene-vinylpyridine copolymer, bromine, copper(II) bromide, a mixture of sodium bromate and bromotrimethylsilane, and combinations thereof. In some embodiments, the brominating agent is 1,3-dibromo-5,5-dimethylhydantoin. Some useful brominating agents have been described in, for example, Baldwin et al., *Synthetic Commun.*, 1976, 6(2), 109; Lee et al., *Bull. Korean. Chem. Soc.*, 1995, 16, 371; Stephenson, *Org. Synth.*, 1963, Collective Vol. 4, 984; Pizey, *Synthetic Reagent*, Halsted Press, New York, 1974, Vol. 2, 1-63; Sket et al., *J. Org. Chem.*, 1986, 51, 929; and Chaintreau et al., *Synth. Comm.*, 1981, 11, 669, all of which are incorporated herein by reference.

Optionally, the benzylic bromination reaction between Formula (IV) and the brominating agent can occur in the presence of a free radical initiator. A free radical is generally an atom or group of atoms that has at least one unpaired electron. A free radical initiator is generally a substance that is capable of initiating the production of free radicals. Any free radical initiator known in the art can be used for the benzylic bromination reaction between Formula (IV) and the brominating agent. Non-limiting examples of suitable free radical initiators include azo compounds, dialkyl peroxides, hydroperoxides, organic polyoxides, diacyl peroxides, peroxy esters, polyatomic peroxides, organometallic peroxides and combinations thereof. Some free radical initiators have been described in Denisov et al, *Handbook of Free Radical Initiators*, 2003, John Wiley & Sons, Inc., Hoboken, N.J., which is incorporated herein by reference. In some embodiments, the free radical initiator is 2,2'-azobisisobutyronitrile, 2,2'-azobis(2,4-dimethylvaleronitrile), 2,2'-azobis(methoxydimethylvaleronitrile), 2,2'-azobis(2-methylbutyronitrile), 1,1'-azobis(cyanocyclohexane), 4,4'-azobis(4-cyanovaleric acid) or benzoyl peroxide, all of the which can be purchased from a supplier such as Dupont and Aldrich Chemicals; or can be prepared according to known synthetic methods. In a particular embodiment, the free radical initiator is 2,2'-azobisisobutyronitrile.

The ratio of the free radical initiator to the brominating agent can be any mole ratio useful for the benzylic bromination reaction between the brominating agent and Formula (IV) according to a person of ordinary skill in the art. For instance, in certain embodiments, the mole ratio of the free radical initiator to the brominating agent can be between about 0.01:1 and about 0.5:1. In other embodiments, the mole ratio of the free radical initiator to the brominating agent is between about 0.05:1 and about 0.25:1. In further embodiments, the mole ratio of the free radical initiator to the brominating agent is between about 0.07:1 and about 0.15:1.

The reaction temperature can be any temperature useful for the reaction between the brominating agent and Formula (IV) according to a person of ordinary skill in the art. For instance, in certain embodiments, the reaction temperature is between about 20° C. and about 120° C. In some embodiments of interest, the reaction temperature is between about 40° C. and about 90° C. In other embodiments of interest, the reaction temperature is between about 50° C. and about 70° C. In a particular embodiment, the solvent is methyl acetate and the reaction temperature is the refluxing temperature of methyl acetate, i.e., between about 55 and 60° C.

The reaction time can be any time useful for the reaction between the brominating agent and Formula (IV) according to a person of ordinary skill in the art. In general, the higher the reaction temperature, the shorter is the reaction time. For instance, in certain embodiments, the reaction time is between about 1 and about 24 hours. In some embodiments of interest, the reaction time is between about 1 and about 10 hours. In a particular embodiment of interest, the reaction time is about 6 to 8 hours at between about 55 and 60° C.

The ratio of the brominating agent to Formula (IV) can be any mole ratio useful for the reaction between the brominating agent and Formula (IV) according to a person of ordinary skill in the art. For instance, in certain embodiments, the mole ratio of the brominating agent to Formula (IV) is between about 0.5:1 and about 1.5:1. In other embodiments, the mole ratio is between 0.75:1 and about 1:1. In further embodiments, the mole ratio is between 0.55:1 and about 0.75:1.

The benzylic bromination reaction can occur in a solvent. Any solvent that does not react with the brominating agent can be used. Non-limiting examples of suitable solvents include methyl acetate, acetonitrile, ethyl acetate, ethers such as diethyl ether and tetrahydrofuran, dichloromethane, chloroform, N-methyl pyrrolidinone, dimethyl formamide, dimethyl sulfoxide, and combinations thereof.

In some embodiments of the 2-methylbenzoic acid ester of Formula (IV), each of $X^2$, $X^3$ and $X^4$ is hydrogen; and $X^1$ is nitro, —$NH_2$ or —$NHCOR^{6'}$ where $R^{6'}$ is hydrogen, alkyl of 1 to 8 carbon atoms, cycloalkyl of 3 to 8 carbon atoms, or phenyl. In other embodiments, $X^1$ is —$NHCOR^{6'}$ and $R^{6'}$ is cyclopropyl. In further embodiments, R is methyl.

A particular embodiment of the 2-methylbenzoic acid ester of Formula (IV) is Compound (3), i.e., methyl 2-bromomethyl-6-nitrobenzoate where $X^1$ is nitro; each of $X^2$, $X^3$ and $X^4$ is hydrogen; R is methyl. Referring to Scheme 13 below, Compound (3) can be prepared from reaction between Compound (4) (i.e., methyl 2-methyl-6-nitrobenzoate) and 1,3-dibromo-5,5-dimethylhydantoin (DBH) in the presence of a free radical initiator such as 2,2'-azobisisobutyronitrile (AIBN) in methyl acetate. In a particular embodiment, the mole ratio of Compound (4) to DBH to AIBN is about 1.02 to about 0.57 to about 0.05.

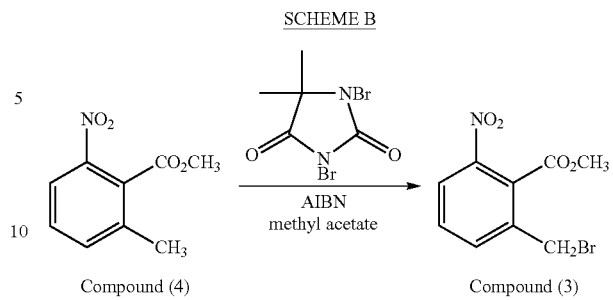

SCHEME B

Compound (4)  Compound (3)

The 2-methylbenzoic acid ester of Formula (IV) can be purchased from a commercial supplier or prepared by reacting an esterification agent with a 2-methylbenzoic acid of Formula (V):

(V)

wherein $X^1$, $X^2$, $X^3$ and $X^4$ are defined as above.

Any esterification agent that can convert the —$CO_2H$ group of Formula (V) into a —$CO_2R$ group can be used for the esterification reaction. In some embodiments, the esterification reaction can be catalyzed or promoted with Bronsted acids, Lewis acids, ion exchange resins, zeolites and the like. In other embodiments, the esterification reaction can be catalyzed or promoted with a base catalyst such as amines, metal carbonates, metal hydrogen carbonates, metal hydroxides and the like. Non-limiting examples of suitable esterification agent include alcohols, metal alkoxides, esters, alkyl halides, diazomethane and orthoesters. The esterifications of acids to form esters have been described in Junzo Otera, "*Esterification: Methods, Reactions, and Applications,*" Wiley-VCH Verlag GmbH & Co. KGaA, Weinheim, p. 3-174, (2003), which is incorporated herein by reference. The esterification of carboxylic acids with orthoesters has been described in the literature such as Yoshino et al., *Synlett,* 2004, 9, 1604; and Trujillo et al., *Tetrahedron Lett.,* 1993, 34, 7355, both of which are incorporated herein by reference. Non-limiting examples of suitable orthoesters include trimethyl orthoacetate, trimethyl orthoformate, triethyl orthoformate, triethyl orthoacetate, triethyl orthopropionate and the like. In some embodiments, the esterification agent is an orthoester. In further embodiments, the orthoester is trimethyl orthoacetate.

The reaction temperature of the esterification can be any temperature useful for the reaction between the esterification agent and Formula (V) according to a person of ordinary skill in the art. For instance, in certain embodiments, the esterification reaction temperature is between about 0° C. and about 120° C. In some embodiments of interest, the esterification reaction temperature is between about 20° C. and about 100° C. In other embodiments of interest, the esterification reaction temperature is between about 80° C. and about 120° C. In a particular embodiment, the esterification agent is trimethyl orthoacetate and the reaction temperature is between about 95 and 100° C.

The reaction time can be any time useful for the reaction between the esterification agent and Formula (V) according to a person of ordinary skill in the art. In general, the higher the reaction temperature, the shorter is the reaction time. For instance, in certain embodiments, the reaction time is from about 1 to about 24 hours. In some embodiments of interest, the reaction time is between about 1 and about 10 hours. In a particular embodiment of interest, the esterification agent is trimethyl orthoacetate and the reaction time is about 1 to 2 hours at between about 95 and 100° C.

The ratio of the esterification agent to Formula (V) can be any mole ratio useful for the esterification reaction according to a person of ordinary skill in the art. For instance, in certain embodiments, the mole ratio of the esterification agent to Formula (V) is between about 2:1 and about 0.5:1. In other embodiments, the mole ratio is between 1.75:1 and about 0.75:1. In further embodiments, the mole ratio is between 1.5:1 and about 1:1.

The esterification reaction can occur in the absence or presence of a solvent. In some embodiments, the esterification reaction occurs in the absence of a solvent. In other embodiments, the esterification reaction occurs in the presence of a solvent. Any solvent that does not react with the esterification agent can be used. Non-limiting examples of suitable solvents include methyl acetate, acetonitrile, ethyl acetate, ethers such as diethyl ether and tetrahydrofuran, dichloromethane, chloroform, N-methyl pyrrolidinone, dimethyl formamide, dimethyl sulfoxide, ionic liquids and combinations thereof In general, an ionic liquid can be any organic salt with a low melting point, preferably lower than 100° C., and more preferably lower than room temperature. It has been reported that the use of an ionic liquid as the solvent can improve the yield of esterification reactions. Non-limiting examples of suitable ionic liquids include halogen-free ionic liquids (e.g., 1-ethyl-3-methylimidazolium tosylate, 1-butyl-3-methylimidazolium octyl sulfate, and 1-butyl-3-methylimidazolium 2-(2-methoxyethoxy)ethyl sulfate), imidazolium compounds (e.g., 1-ethyl-3-methylimidazolium bromide, 1-ethyl-3-methylimidazolium hexafluorophosphate, and 1-butyl-3-methylimidazolium hexafluorophosphate) and pyridinium compounds (e.g., 1-Butyl-4-methylpyridinium chloride and 1-butyl-4-methylpyridinium hexafluorophosphate), phosphonium compounds, tetraalkylammonium compounds, and combinations thereof. Some ionic liquids are described in Wasserscheid et al., *Angew. Chem. Int. Ed.* 2000, 39, 3772; Welton, *Chem. Rev.* 1999, 99, 2071; Sheldon, *Chem. Commun.* 2001, 2399; and Dupont et al., *Chem. Rev.* 2002, 102, 3667, all of which are incorporated herein by reference.

In some embodiments of the 2-methylbenzoic acid ester of Formula (V), each of $X^2$, $X^3$ and $X^4$ is hydrogen; and $X^1$ is nitro, $-NH_2$ or $-NHCOR^{6'}$ where $R^{6'}$ is hydrogen, alkyl of 1 to 8 carbon atoms, cycloalkyl of 3 to 8 carbon atoms, or phenyl. In other embodiments, $X^1$ is $-NHCOR^{6'}$ and $R^{6'}$ is cyclopropyl.

In a particular embodiment, the 2-methylbenzoic acid ester of Formula (IV) is Compound (4), i.e., methyl 2-methyl-6-nitrobenzoate where $X^1$ is nitro; each of $X^2$, $X^3$ and $X^4$ is hydrogen; R is methyl. Referring to Scheme C below, Compound (4) can be prepared from reaction between Compound (5) (i.e., 2-methyl-6-nitrobenzoic acid) and trimethyl orthoacetate in the absence of a solvent or catalyst. The reaction temperature between trimethyl orthoacetate and the 2-methylbenzoic acid of Formula (V) can be between about 80 and about 120° C. The mole ratio of trimethyl orthoacetate to Formula (V) can be between about 1:1 and about 2:1. In a particular embodiment, the reaction temperature is between about 95 and about 100° C. and the mole ratio of trimethyl orthoacetate to Formula (V) is about 1.5:1.

SCHEME C

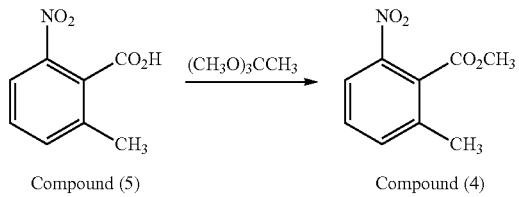

Compound (5)    Compound (4)

In one particular embodiment, the isoindolin-1-one compound of Formula (I) is a 7-nitroisoindolin-1-one compound having the following formula:

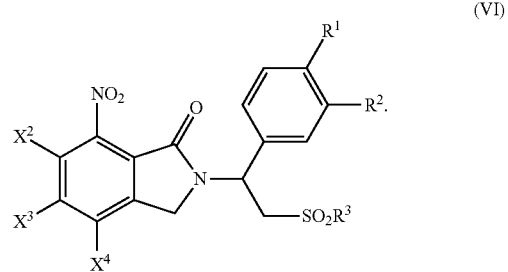

(VI)

where $X^2$, $X^3$, $X^4$, $R^1$, $R^2$ and $R^3$ are defined as above. In some embodiments, each of $X^2$, $X^3$ and $X^4$ is hydrogen; each of $R^1$ and $R^2$ is independently alkoxy of 1 to 4 carbon atoms; and $R^3$ is alkyl of 1 to 8 carbon atoms. In a further embodiment, $R^1$ is methoxy; $R^2$ is ethoxy; and $R^3$ is methyl.

In another embodiment, the isoindolin-1-one compound of Formula (I) is a 7-aminoisoindolin-1-one compound having the following formula:

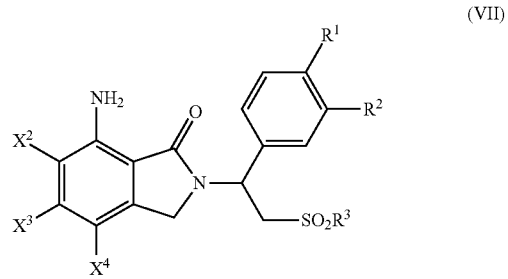

(VII)

where $X^2$ $X^3$, $X^4$, $R^1$, $R^2$ and $R^3$ are defined as above. The 7-aminoisoindolin-1-one compound of Formula (VII) can be prepared by reacting the primary amine of Formula (II) with the 2-(bromomethyl)benzoic acid ester of Formula (III) where $X^1$ is $-NH_2$. In general, the primary amine group of Formula (II) is more reactive than the aromatic amine group of Formula (VII) in nucleophilic substitution reactions. However, if it is necessary, the aromatic amine group of Formula (VII) can be protected by a protecting group before the reaction and removed later after the reaction. Any amine protecting group known to a person of ordinary skill in the art can be used. Non-limiting examples of suitable amine protecting groups include acyl groups (e.g., formyl, acetyl, and benzoyl), urea and urethane derivatives, and alkyl and aryl derivatives. Some amine protecting group are described in Jif MacOmie, "Protective Groups in Organic Chemistry," Plenum Pub. Corp., Chapter 2 (1973), which is incorporated herein by reference. The reaction between Formula (II) and Formula (III) has been discussed above.

Alternatively, the 7-aminoisoindolin-1-one compound of Formula (VII) can be prepared by reducing the 7-nitroisoindolin-1-one compound of Formula (VI) with a reducing agent. The reducing agent can be any known reducing agent in the art that can reduce a nitro group to a primary amine. Non-limiting examples of such reducing agents include hydrogen plus a catalyst (catalytic hydrogenation), reducing metals in an acid such as hydrochloric acid and acetic acid, sodium sulfide in ammonium hydroxide solution, zinc in ammonium formate solution, magnesium in hydrazinium monoformate solution and tin dichloride in dilute hydrochloric acid. Non-limiting examples of suitable hydrogenation catalyst include palladium (Pd) and platinum (Pt). Non-limiting examples of suitable reducing metals include iron, zinc amalgam, zinc and tin. In a particular embodiment, the reducing agent is hydrogen plus a catalyst. In a further embodiment, the catalyst is a Pd catalyst. In another embodiment, the catalyst is 5% Pd/C. In another embodiment, the catalyst is 10% Pd/C.

The catalytic hydrogenation is generally carried out at a hydrogen pressure that drives the reaction to substantial completion. In a particular embodiment, the catalytic hydrogenation is carried out at a hydrogen pressure between about 2.7 and 3.5 bars (about 40 and 50 psi or about 5332 and 6666 pascals).

In one embodiment, the catalytic hydrogenation is run at ambient temperature. The catalytic hydrogenation is generally performed until the reaction is substantially complete. In a particular embodiment, the catalytic hydrogenation is performed for about 1-24 hours at a temperature between about 15° C. and about 50° C. In a further embodiment, the catalytic hydrogenation is performed for about 4-6 hours at about 35-45° C.

The catalytic hydrogenation can occur in a solvent. In one embodiment, the catalytic hydrogenation is conducted in a protic solvent, such as alcohols, water, and combinations thereof In a further embodiment, the alcohol solvent is selected from the group consisting of methanol, ethanol, propanol, isopropanol, butanol, isobutanol, t-butanol and combinations thereof In another embodiment, the catalytic hydrogenation is conducted in an apolar, aprotic solvent such as 1,4-dioxane. In yet another embodiment, the catalytic hydrogenation is conducted in a polar, aprotic solvent such as ethyl acetate, acetonitrile, acetone, DMSO, DMF and THF. In one embodiment of interest, the solvent is a protic solvent. In a further embodiment of interest, the solvent for catalytic hydrogenation is ethyl acetate.

In some embodiments of the 7-aminoisoindolin-1-one compound of Formula (VII), each of $X^2$, $X^3$ and $X^4$ is hydrogen. In other embodiments, each of $R^1$ and $R^2$ is independently alkoxy of 1 to 4 carbon atoms; and $R^3$ is alkyl of 1 to 8 carbon atoms. In other embodiments, $R^1$ is methoxy and $R^2$ is ethoxy. In further embodiments, $R^3$ is methyl.

In a particular embodiment, the 7-aminoisoindolin-1-one compound of Formula (VII) is Compound (6) where $X^1$ is —$NH_2$; each of $X^2$, $X^3$ and $X^4$ is hydrogen; $R^1$ is methoxy; $R^2$ is ethoxy; and $R^3$ is methyl. Referring to Scheme D below, Compound (6) can be prepared by reducing Compound (1) with hydrogen in the presence of 10% Pd/C catalyst. The catalytic hydrogenation can occur at about 40° C. for about 4-6 hours in ethyl acetate in the presence of 10% Pd/C. In a further embodiment, the catalytic hydrogenation occurs at a hydrogen pressure between about 40 and 45 psi or 2.7 to 3.1 bars.

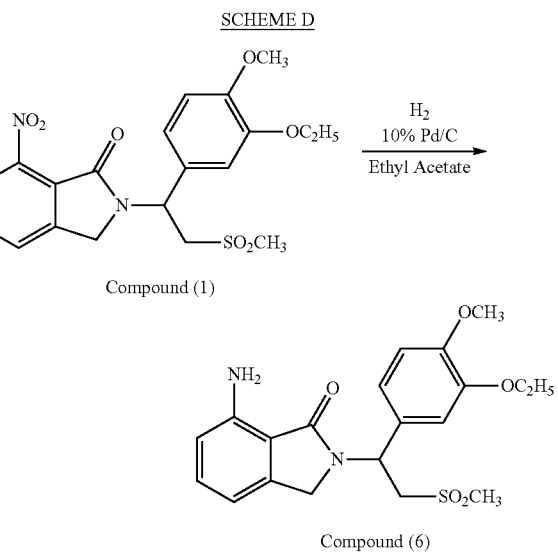

SCHEME D

Compound (1)

Compound (6)

If a racemic mixture of compound (6) is desired, a racemic mixture of Compound (1) can be used. Conversely, if an enantiomerically pure compound (6) is desired, an enantiomerically pure Compound (1) can be used. Alternatively, if an enantiomerically pure compound (6) is desired, a racemic mixture of Compound (6) can be prepared and then resolved into the enantiomers by conventional resolution techniques such as biological resolution and chemical resolution. In one embodiment, compound (6) is a racemic mixture. In another embodiment, compound (6) is the (+)-enantiomer. In a further embodiment, compound (6) is the (−)-enantiomer.

Optionally, the 7-aminoisoindolin-1-one compound of Formula (VII) can be converted into an acid salt by reacting Formula (VII) with an acid in a mole ratio of 1:1. Non-limiting examples of suitable acid include methanesulfonic acid, trifluoroacetic acid, 4-(trifluoromethyl)benzoic acid, p-toluenesulfonic acid, hydrochloric acid, nitric acid, sulfuric acid and phosphoric acid. In one embodiment, Formula (VII) is converted into a hydrochloride salt with 12N hydrochloric acid at a temperature between 0° C. and 22° C.

In another embodiment, the compound of Formula (I) is an amide compound having the following formula:

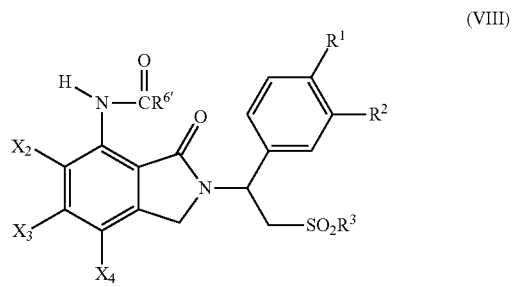

(VIII)

where $X^2$, $X^3$, $X^4$, $R^1$, $R^2$ and $R^3$ are defined as above; and $R^{6'}$ is alkyl of 1 to 8 carbon atoms, cycloalkyl of 3 to 8 carbon atoms, or phenyl. The amide compound of Formula (VIII) can be prepared by reacting the primary amine of Formula (II) with the 2-(bromomethyl)benzoic acid ester of Formula (III) where $X^1$ is —NHCOR$^6$. The reaction between Formula (II) and Formula (III) has been discussed above.

Alternatively, the amide compound of Formula (VIII) can be prepared by reacting the 7-aminoisoindolin-1-one of Formula (VII) or its acid salt with an acyl halide having the formula $R^{6'}$—C(O)-Ha where $R^{6'}$ is defined as above and Ha is F, Cl, Br or I. The reaction between the compound of Formula (VII) or its acid salt and the acyl halide can occur in a solvent, such as ethyl acetate, acetone, methyl ethyl ketone, diethyl ether, tetrahydrofuran, acetonitrile, dichloromethane, chloroform, N-methyl pyrrolidinone, dimethyl formamide, dimethyl sulfoxide and mixture thereof. In one embodiment, the solvent is ethyl acetate.

The reaction temperature of the acylation reaction can be any temperature useful for the acylation reaction according to a person of ordinary skill in the art. For instance, in certain embodiments, the reaction temperature of the acylation reaction between the acyl halide and Formula (VII) or its acid salt can be between about 0° C. and about 50° C. In one embodiment of interest, the reaction temperature is between about 15° C. and about 25° C.

Optionally, the acylation reaction can occur in the presence of a base catalyst, such as organic amines. Non-limiting examples of organic amines include triethylamine, N,N-diisopropylethylamine, pyridine and DBU, imidazole, and combinations thereof. In one embodiment of interest, the catalyst is triethylamine. In another embodiment of interest, the catalyst is imidazole. In a further embodiment of interest, the catalyst is N,N-diisopropylethylamine.

The reaction time of the acylation reaction can be any time period useful for the acylation reaction according to a person of ordinary skill in the art. In general, the higher the reaction temperature, the shorter is the reaction time. For instance, in certain embodiments, the reaction time of the acylation reaction varies from 1 to 24 hours. In one embodiment of interest, the reaction time is between about 4 and about 6 hours at a reaction temperature between 20° C. and 25° C.

In one embodiment, the acyl halide is added to a solution of the compound of Formula (VII), followed by the addition of a base catalyst. In another embodiment, the base catalyst is added to a solution of the compound of Formula (VII), followed by the addition of the acyl halide. In another embodiment, the mole ratio of the base catalyst to the compound of Formula (VII) is between about 2:1 and about 1:2. In an additional embodiment, the mole ratio is between about 1.4:1 and about 1:1.

In general, any acyl halide that can react with a primary amine or a secondary amine can be used for this embodiment. Non-limiting examples of suitable acyl halides include cyclopropanecarbonyl chloride, cyclobutanecarbonyl chloride, cyclopentanecarbonyl chloride, cyclohexanecarbonyl chloride, cyclopentylacetyl chloride, 1-methylcyclohexanecarbonyl chloride, 3-cyclopentylpropanoyl chloride, and cycloheptanecarbonyl chloride, all of which can be obtained commercially from a supplier, such as Aldrich Chemicals, Milwaukee, Wis. or be prepared by halogenating the corresponding carboxylic acids ($R^{6'}$COOH where $R^{6'}$ is defined as above) with a halogenating agent. The halogenating agent can be PY$_3$, PY$_5$ or SOY$_2$ where Y can be F, Cl, Br or I. For example, an acyl chloride (such as cycloheptanecarbonyl chloride) can be prepared by reacting the corresponding carboxylic acid (cycloheptanecarboxylic acid) with SOCl$_2$ or PCl$_5$. Similarly, an acyl bromide can be prepared by reacting the corresponding carboxylic acid with PBr$_5$.

The ratio of the acyl halide to Formula (VII) can be any mole ratio useful for the acylation reaction according to a person of ordinary skill in the art. For instance, in certain embodiments, the mole ratio of the acyl halide to Formula (VII) is between about 2:1 and about 0.5:1. In other embodiments, the mole ratio is between about 1.75:1 and about 0.75:1. In further embodiments, the mole ratio is between about 1.2:1 and about 1:1.

The acylated compound of Formula (VIII) can be purified by recrystallization with a solvent. In one embodiment, the solvent is tetrahydrofuran, ethanol, N-methyl pyrrolidinone, methanol, ethyl acetate, isopropanol, acetic acid, water or a combination thereof. In a further embodiment, the solvent is a mixture of tetrahydrofuran and ethanol in a volume ratio of 3:1 to 1:3.

In some embodiments of the amide compound of Formula (VIII), $R^6$ is cycloalkyl of 3 to 8 carbon atoms. In further embodiments, $R^6$ is cyclopropyl. In other embodiments, each of $R^1$ and $R^2$ is independently alkoxy of 1 to 4 carbon atoms; and $R^3$ is alkyl of 1 to 8 carbon atoms. In further embodiments, $R^1$ is methoxy and $R^2$ is ethoxy. In other embodiments, each of $X^2$, $X^3$ and $X^4$ is hydrogen. In other embodiments, $R^3$ is methyl.

In a particular embodiment, the amide compound of Formula (VIII) is Compound (7) where $X^1$ is —NHCO-cyclopropyl; each of $X^2$, $X^3$ and $X^4$ is hydrogen; $R^1$ is methoxy; $R^2$ is ethoxy; and $R^3$ is methyl. Referring to Scheme E below, Compound (7) can be prepared, for example, by reacting Compound (6) with cyclopropylcarbonyl chloride in the presence of N,N-diisopropylethylamine. The acylation reaction can occur, for example, at a reaction temperature between 20° C. and 25° C. for about 4 and about 6 hours in ethyl acetate. The mole ratio of Compound (6) to cyclopropylcarbonyl chloride to N,N-diisopropylethylamine is about 1:1.05:1.2.

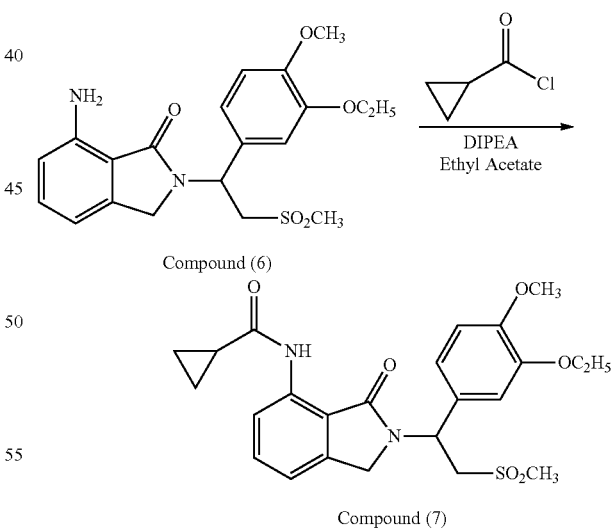

SCHEME E

Compound (6)

Compound (7)

If a racemic mixture of compound (7) is desired, a racemic mixture of Compound (6) can be used. Conversely, if an enantiomerically pure compound (7) is desired, an enantiomerically pure Compound (6) can be used. Alternatively, if an enantiomerically pure compound (7) is desired, a racemic mixture of Compound (7) can be prepared and then resolved into the enantiomers by conventional resolution techniques such as biological resolution and chemical resolution.

The isoindolin-1-one compounds of Formula (I) can be used to prepare pharmaceutical compositions for treating a wide range of diseases and conditions including, but not limiting to, inflammatory diseases, autoimmune diseases, cancers, heart diseases, genetic diseases, allergic diseases, osteoporosis and lupus.

In general, the pharmaceutical compositions can comprise at least an isoindolin-1-one compound of Formula (I) or a pharmaceutically acceptable salt, solvate or stereoisomer thereof can be administered to patients to be treated for a wide range of diseases and conditions.

Optionally, the pharmaceutical compositions and dosage forms can further comprise one or more carriers, excipients, diluents or active agents. In some embodiments, the pharmaceutical compositions can be used in the preparation of individual, single unit dosage forms. Single unit dosage forms are suitable for oral, mucosal (e.g., sublingual, nasal, vaginal, cystic, rectal, preputial, ocular, buccal or aural), parenteral (e.g., subcutaneous, intravenous, bolus injection, intramuscular or intraarterial), topical (e.g., eye drops or other ophthalmic preparations), transdermal or transcutaneous administration to a patient. Non-limiting examples of dosage forms include tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

Particular embodiments provided herein are illustrated by the syntheses of 7-nitro-2-[1-(3-ethoxy-4-methoxyphenyl)-2-(methylsulfonyl)ethyl]isoindolin-1-one and cyclopropyl-N-{2-[1-(3-ethoxy-4-methoxyphenyl)-2-(methylsulfonyp-ethyl]-3-oxoisoindolin-4-yl}carboxamide. Modifications of variables including, but not limited to, reaction solvents, reaction times, reaction temperatures, reagents, starting materials, and functional groups in the particular embodiments of the synthesis of 7-nitro-2-[1-(3-ethoxy-4-methoxyphenyl)-2-(methylsulfonyl)ethyl]isoindolin-1-one and cyclopropyl-N-{2-[1-(3-ethoxy-4-methoxyphenyl)-2-(methylsulfonyl)ethyl]-3-oxoisoindolin-4-yl}carboxamide will be apparent to those of ordinary skill in the art.

5. EXAMPLES

Example 1

Preparation of Methyl 2-Methyl-6-nitrobenzoate

A mixture of 2-methyl-6-nitrobenzoic acid (300.0 g, 1.66 moles, from Acros Organics, Morris Plains, N.J.) and trimethyl orthoacetate (298.3 g, 2.48 moles, from Aldrich Chemicals, Milwauke, Wis.) was charged into a 3-L 3-necked flask at about 20-25° C. under nitrogen. The reaction mixture was gradually heated and the low-boiling point components generated during the reaction were distilled off to an internal temperature of 95-100° C. After 2 hours, the reaction mixture was cooled to 20-25° C. over 1-2 hours. After heptane (1.50 L, from Aldrich Chemicals) was charged into the reaction mixture over 1.0-1.5 hours, the reaction mixture was seeded with methyl 2-methyl-6-nitrobenzoate (0.5 g) when it became turbid. The suspension was cooled to 0-5° C. over 0.5-1 hour and kept at 0-5° C. for another 1.5-2 hours. The solid was collected by filtration under vacuum, washed with heptane (3×300 mL), and dried to a constant weight in a tray at 30-35° C. under a vacuum at 100-120 torr. The yield of methyl 2-methyl-6-nitrobenzoate was 292.0 g (91%), based on 300.0 g of 2-methyl-6-nitrobenzoic acid. The product was found to have a purity of >99% measured by HPLC based on area percentage, and a water content of <0.1% measured by Karl Fisher titration.

Example 2

Preparation of Methyl 2-Bromomethyl-6-nitrobenzoate

A mixture of methyl 2-methyl-6-nitrobenzoate (200.0 g, 1.02 moles, previously prepared), 1,3-dibromo-5,5-dimethylhydantoin (DBH, 162.0 g, 0.57 mole, from Aldrich Chemicals) and methyl acetate (1.20 L, from Aldrich Chemicals) was charged into a 3-L three-necked flask at about 20-25° C. under nitrogen. After the reaction mixture was refluxed for 0.5-1 hour, a solution of 2,2'-azobisisobutyronitrile (AIBN, 8.6 g, 52 mmol, from Aldrich Chemicals) in 100 mL of methyl acetate was charged over 15-30 minutes. The reaction mixture was refluxed for 6.5-8 hours until the amount of unreacted 2-methyl-6-nitrobenzoate was less than 5-10%. The reaction mixture was cooled to 15-18° C. and kept at 15-18° C. for 50-60 minutes. The solid was filtered, washed with cold (i.e., 5-10° C.) methyl acetate (2×100 mL) until there was less than 3% of methyl 2-bromomethyl-6-nitrobenzoate remained in the solid. Next, after heptane (1.00 L) was charged into the filtrate, the upper layer organic phase was washed with 2% of brine (2×500 mL) and deionized water (1-2×500 mL) until there was less than 0.5% (area percentage at 210 nm) of unreacted 5,5-dimethylhydantoin according to measurement by HPLC. After the solution was concentrated under a reduced pressure to remove about 1.80-1.90 L of methyl acetate, methyl tert-butyl ether (MTBE, 300 mL) was charged. After the reaction mixture was refluxed at 65-70° C. for 10-15 minutes, the solution was cooled to 50-55° C. over 0.5-1 hour and seeded with 500 mg of methyl 2-bromomethyl-6-nitrobenzoate at 45-50° C. The suspension was cooled to 20-25° C. and kept at 20-25° C. for 2-3 hours. The solids were collected by filtration, washed with 5-10° C. a cold mixture of heptane and MTBE in a volume ratio of 1:2 (2×100 mL), and dried to a constant weight at 20-25° C. under a vacuum at 100-120 ton. The yield of methyl 2-bromomethyl-6-nitrobenzoate was 185.2 g (66%), based on 200.0 g input of methyl 2-methyl-6-nitrobenzoate. The product was found to have a purity of >98% measured by HPLC based on area percentage, and a water content of <0.1% measured by Karl Fisher titration.

Example 3

Preparation of (1S)-1-(3-Ethoxy-4-methoxyphenyl)-2-methanesulfonyl-ethylamine

After a mixture of (1S)-1-(3-ethoxy-4-methoxyphenyl)-2-methanesulfonyl-ethylamine N-acetyl-L-Leucine salt (1.10 kg, 2.46 moles), deionized water (4.40 L), and dichloromethane (DCM, 5.50 L) was charged into a reaction vessel, a solution of sodium hydroxide (196.0 g, 4.90 moles) in 1.00 L of deionized water was charged into the reaction vessel over about 5 minutes at 15-25° C. The resulting mixture was stirred for at least 10 minutes at 15-25° C. and then the aqueous and organic phases were allowed to separate. The pH of the upper aqueous phase was maintained or adjusted at pH 13-14. The phases were separated and the upper aqueous phase was extracted with DCM (2×4.4 L). The pH of the aqueous phase was maintained at 13-14 throughout the extractions. The DCM extracts were combined and washed with deionized water (3.3 L) until the pH of the aqueous phase reached 11 or less. DCM was removed under vacuum below 35° C. The water content of the residual solid should be <0.1% w/w as measured by Karl Fisher titration. The residual solid was dried azeotropically with more DCM. The solid was dried to a constant weight in vacuo at 30-35° C. to give (1S)-1-(3-ethoxy-4-methoxyphenyl)-2-methanesulfonyl-ethylamine as a white powder (639.0-672.0 g, 95-100% yield).

Example 4A

Preparation of Compound (1)

Compound (1) was prepared by the following procedure. A mixture of methyl 2-bromomethyl-6-nitrobenzoate (100.0 g, 365 mmol, prepared previously in Example 2), (1S)-1-(3-ethoxy-4-methoxyphenyl)-2-methanesulfonylethylamine (104.7 g, 383 mmol, prepared previously in Example 3), sodium hydrogen carbonate (67.5 g, 8.03 moles, from Aldrich Chemicals) and dimethyl formamide (500 mL) was charged into a 1-L 3-necked flask at room temperature under nitrogen. The reaction mixture was gradually heated to an internal temperature of 70-75° C. for two hours until there was less than <2% of unreacted methyl 2-bromomethyl-6-nitrobenzoate. The reaction mixture was gradually heated to an internal temperature of 95-100° C. for 18 hours. The reaction mixture was cooled to 20-25° C. and transferred to an 1-L addition funnel. After purified water (1500 mL) was charged into a 5-L 3-necked flask, the reaction mixture in the addition funnel was added into water in the 5-L 3-necked flask at room temperature over 1-2 hours maintaining an internal temperature below 30° C. The reaction mixture was stirred for 2 hours at room temperature. The solid was filtered out under vacuum, washed with water (3×300 mL) and methanol (2×400 mL), and then charged into a 2-L 3-necked flask followed by methanol (1000 mL). The mixture was refluxed for 1 hour. The mixture was cooled to room temperature. The solid was collected by filtration under vacuum, washed with 200 mL methanol (2 vol), and dried to a constant weight at 40-45° C. under a vacuum at 100-120 torr. The yield of Compound (1) was 123.0 g (78%), based on 100.0 g input of methyl 2-bromomethyl-6-nitrobenzoate. The product was found to have a purity of >99% measured by HPLC based on area percentage, and a water content of <0.1% measured by Karl Fisher titration.

Example 4B

Alternative Preparation of Compound (1)

Compound (1) was also prepared by the following procedure. A mixture of methyl 2-bromomethyl-6-nitrobenzoate (100.0 g, 365 mmol, prepared previously in Example 2), (1S)-1-(3-ethoxy-4-methoxyphenyl)-2-methanesulfonyl-ethylamine (104.7 g, 383 mmol, prepared previously in Example 3), and potassium carbonate powder (100.8 g, 730 mmol, from Aldrich Chemicals) was suspended in acetonitrile (500 mL) at room temperature. The reaction mixture was refluxed at 81-83° C. for about two hours until there was less than 2% of unreacted methyl 2-bromomethyl-6-nitrobenzoate. After the reaction mixture was cooled to 45-50° C., methanol (200 mL) was charged over 5-10 minutes. After the mixture was allowed to cool to 20-25° C. and stirred for 2 hours, deionized water (1.40 L) was charged over 0.5-1 hour and stirred at 20-25° C. for 30 minutes and at 0-5° C. for 1-2 hours. The solid was filtered, washed with deionized water (3×300 mL), and dried to <10% of water content as measured by Karl Fisher titration. The solid was suspended in methanol (750 mL) and refluxed for 1-1.5 hours. The suspension was cooled to 0-5° C. over 1.5-2 hours and kept at 0-5° C. for 1-1.5 hours. The solid was filtered, washed with 0-5° C. methanol (2×200 mL) and heptane (200 mL), and then dried at 40-45° C. under vacuum to a constant weight. The yield of Compound (1) was 148.0 g (93%), based on 100.0 g input of methyl 2-bromomethyl-6-nitrobenzoate. The product was found to have a purity of >99% measured by HPLC based on area percentage, and a water content of <1.0% measured by Karl Fisher titration.

Example 5

Preparation of Compound (7)

A mixture of Compound (1) (60 g, 138 mmol, prepared previously in Example 4, 10% Pd/C (50% wet, 2.4 g, 4 wt %, from Johnson Matthey, London, UK), ethyl acetate (780 mL) was charged into a Parr-vessel at room temperature under nitrogen. After the mixture was purged with nitrogen three times and with hydrogen three times, the reaction mixture was heated to 40° C. and then the heat was removed. The reaction mixture was stirred with hydrogen at a pressure between 40-45 psi over 4-6 hours until there was ≦3% of the hydroxylamine intermediate. The reaction mixture was cooled to 20-25° C. The reaction mixture was filtered through a celite bed (1 inch thickness) and then bed-washed with ethyl acetate (120 mL). The filtrate was transferred to a 3-L 3-necked flask equipped with a 50-mL addition funnel. After N,N-diisopropylethylamine (29 mL, 165 mmol) was charged into the flask, the addition funnel was charged with cyclopropylcarbonyl chloride (13.0 mL, 145 mmol, from Aldrich Chemicals). The cyclopropylcarbonyl chloride was added at room temperature over 1-2 hours at an internal temperature below 30° C. The reaction mixture was stirred for 2-4 hours at room temperature. After heptane (300 mL) was added, the reaction mixture was stirred for 4-6 hours. The solid was collected by filtration under vacuum, washed with 2N HCl (2×300 mL), water (2×300 mL) and then heptane (2×300 mL). The crude product was dried at 40-45° C. under a vacuum at 100-120 torr to a constant weight. The yield of crude Compound (7) was 58 g (88%), based on 60.0 g input of Compound (1).

Example 6

Recrystallization of Compound (7)

A mixture of crude Compound (7) (95.2 g, prepared previously in Example 5) and tetrahydrofuran (THF, 1.43 L) was charged into a 3 L flask at 20-25° C. under nitrogen. The suspension was heated to 60-65° C. until dissolution was achieved. The suspension was filtered at 45-50° C. and the solid was rinsed with 95 mL of THF prewarmed at 45-55° C. After about 950-1150 mL of THF was distilled off at normal pressure over 30-60 minutes, absolute ethanol (950 mL) was charged at 55-60° C. over 5-10 minutes. About 350-400 mL of solvents was removed at normal pressure until the internal temperature rose to 72-74° C. The resulting suspension was refluxed at 72-75° C. for 30-60 minutes, cooled to 20-25° C. over 1-2 hours and kept at 20-25° C. for another 1-2 hours. The solid was collected by filtration under vacuum, washed with absolute ethanol (240-280 mL) and heptane (240-280 mL), and then dried in tray at 50-55° C. in a vacuum at 130-140 ton to a constant weight. The yield of the off-white crystalline product was (88.0-91.0 g, 92-96%).

The present disclosure is not to be limited in scope by the specific embodiments disclosed in the examples that are intended as illustrations, and any embodiments that are functionally equivalent are within the scope provided herein. Indeed, various modifications in addition to those shown and described herein will become apparent to those skilled in the art and are intended to fall within the appended claims.

What is claimed is:

1. A process for preparing a compound of formula:

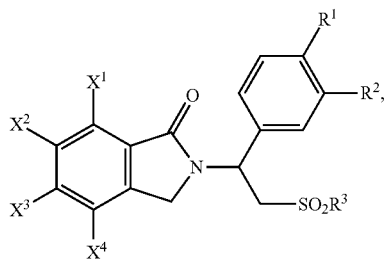

or a pharmaceutically acceptable salt thereof,
comprising the step of reacting a primary amine of formula (II)

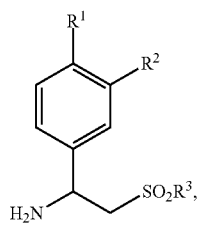

or a salt thereof,
with a 2-(bromomethyl)benzoic acid ester of formula (III):

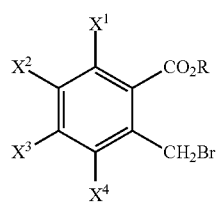

in the presence of an inorganic base, wherein:
R is alkyl or aryl;
each of $R^1$ and $R^2$ is independently hydrogen, alkyl of 1 to 4 carbon atoms, alkoxy of 1 to 4 carbon atoms, cyano, or cycloalkoxy of 3 to 18 carbon atoms;
$R^3$ is hydroxyl, alkyl of 1 to 8 carbon atoms, phenyl, benzyl or $NR^4R^5$;

each of $X^1$, $X^2$, $X^3$ and $X^4$ is independently hydrogen, halo, alkyl of 1 to 4 carbon atoms, alkoxy of 1 to 4 carbon atoms, nitro, cyano, hydroxyl, or —$NR^{4'}R^{5'}$; or
any two of $X^1$, $X^2$, $X^3$ and $X^4$ on adjacent carbon atoms, together with the depicted phenylene ring, form naphthylidiene;
each of $R^4$ and $R^5$ is independently hydrogen, alkyl of 1 to 8 carbon atoms, phenyl, or benzyl; or
one of $R^4$ and $R^5$ is hydrogen, and the other is —$COR^6$, or —$SO_2R^6$; or
$R^4$ and $R^5$ taken together are tetramethylene, pentamethylene, hexamethylene, or —$CH_2CH_2X^5CH_2CH_2$— in which $X^5$ is —O—, —S—, or —NH—;
each of $R^{4'}$ and $R^{5'}$ is independently hydrogen, alkyl of 1 to 8 carbon atoms, phenyl, or benzyl; or
one of $R^{4'}$ and $R^{5'}$ is hydrogen and the other is —$COR^{6'}$, or —$SO_2R^{6'}$; or
$R^{4'}$ and $R^{5'}$ taken together are tetramethylene, pentamethylene, hexamethylene, or —$CH_2CH_2X^{5'}CH_2CH_2$—in which $X^{5'}$ is —O—, —S—, or —NH—; and
each of $R^6$ and $R^{6'}$ is independently hydrogen, alkyl of 1 to 8 carbon atoms, cycloalkyl of 3 to 8 carbon atoms, or phenyl.

2. The process of claim 1, wherein the inorganic base is a metal hydroxide, a metal carbonate, a metal hydrogen carbonate, a metal hydride, or a combination thereof.

3. The process of claim 2, wherein the metal hydroxide is potassium hydroxide or sodium hydroxide.

4. The process of claim 2, wherein the metal carbonate is potassium carbonate or sodium carbonate.

5. The process of claim 2, wherein the metal hydrogen carbonate is potassium hydrogen carbonate or sodium hydrogen carbonate.

6. The process of claim 1, wherein the solvent in which the reaction between (II) and (III) occurs is acetonitrile.

7. The process of claim 6, wherein the reaction temperature is the boiling point of acetonitrile.

8. The process of claim 1, wherein the mole ratio of Formula (III) to Formula (II) is from about 1:0.8 to about 1:1.3.

9. The process of claim 1, wherein an enatiomerically pure (S)-isomer of Formula (II) is used.

10. The process of claim 1, wherein an enatiomerically pure (R)-isomer of Formula (II) is used.

11. The process of claim 1, wherein $X^1$ is nitro.

12. The process of claim 11, further comprising the step of reducing the nitro using a reducing agent to obtain a 7-aminoisoindolin-1-one compound of the following formula (VII):

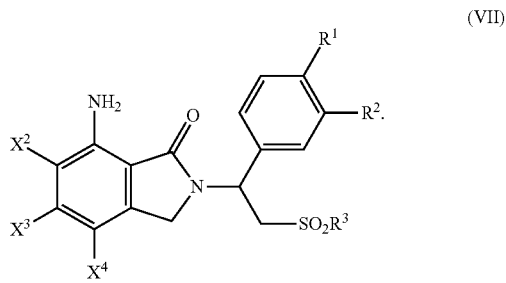

13. The process of claim 12, wherein the reducing agent is Pd/C and hydrogen.

14. The process of claim 12, further comprising the step of reacting Formula (VII) with an acyl halide ($R^{6'}$—C(O)-halogen) to obtain an amide compound of the following foimula (VIII):

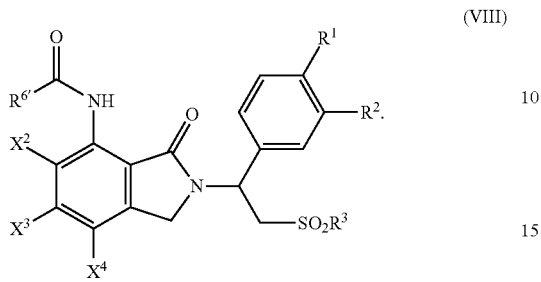

(VIII)

15. The process of claim 14, wherein an enantiomerically pure (S)-isomer of Formula (VII) is used.

16. The process of claim 14, wherein an enantiomerically pure (R)-isomer of Formula (VII) is used.

17. The process of any one of claims 11, 12 and 14-16, wherein $X^2$-$X^4$ are all hydrogen, $R^1$ is methoxy, $R^2$ is ethoxy, and $R^3$ is methyl.

* * * * *